United States Patent [19]

Collins et al.

[11] Patent Number: 4,820,728
[45] Date of Patent: * Apr. 11, 1989

[54] TETRAENYL PROSTAGLANDINS

[75] Inventors: Paul W. Collins, Deerfield; Alan F. Gasiecki, Vernon Hills, both of Ill.

[73] Assignee: G. D. Searle & Co., Chicago, Ill.

[*] Notice: The portion of the term of this patent subsequent to Jul. 28, 2004 has been disclaimed.

[21] Appl. No.: 68,608

[22] Filed: Jun. 30, 1987

Related U.S. Application Data

[63] Continuation of Ser. No. 801,370, Nov. 25, 1985, Pat. No. 4,683,328.

[51] Int. Cl.$^4$ .................. C07C 177/00; A01K 31/557
[52] U.S. Cl. ..................... 514/530; 514/573; 560/118; 562/500
[58] Field of Search ............... 514/530, 573; 560/118; 562/500

[56] References Cited

U.S. PATENT DOCUMENTS

| | | | |
|---|---|---|---|
| 3,965,143 | 6/1976 | Collins | 560/112 |
| 4,499,296 | 2/1985 | Collins | 560/118 |
| 4,536,592 | 8/1985 | Collins | 560/53 |
| 4,683,328 | 7/1987 | Collins | 560/118 |

FOREIGN PATENT DOCUMENTS 84113676.5 5/1985 European Pat. Off.
1492426 11/1977 United Kingdom.

Primary Examiner—Robert Gerstl
Attorney, Agent, or Firm—Mary Jo Kanady; Paul D. Matukaitis

[57] ABSTRACT

This invention encompasses prostaglandins of the formula

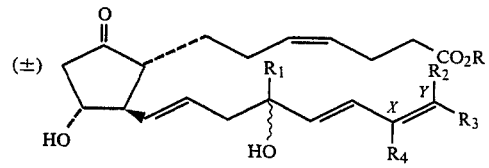

wherein R represents hydrogen or lower alkyl having 1 to 6 carbon atoms; $R_1$ represents hydrogen, vinyl, or lower alkyl having 1 to 4 carbon atoms and the wavy line represents R or S stereochemistry; $R_2$, $R_3$, and $R_4$ are hydrogen or lower alkyl having 1 to 4 carbom atoms or $R_2$ and $R_3$ together with carbon Y form a cycloalkenyl having 4 to 6 carbon atoms or $R_3$ and $R_4$ together with carbons X and Y form a cycloalkenyl having 4 to 6 carbons. Compounds of this invention have potent gastric antisecretory and cytoprotective properties with unexpectedly low diarrheogenic side effects.

3 Claims, No Drawings

TETRAENYL PROSTAGLANDINS

This is a continuation of application Ser. No. 06/801,370, filed Nov. 25, 1985, now U.S. Pat. No. 4,683,328.

BACKGROUND OF THE INVENTION

U.S. Pat. No. 3,965,143 generally describes compounds of the formula

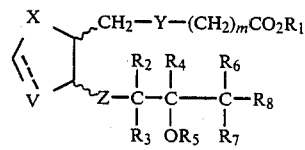

wherein $R_1$, $R_2$, $R_3$, $R_4$, $R_6$ and $R_7$ can be hydrogen or a lower alkyl radical, $R_5$ can be hydrogen or a lower alkanoyl, tetrahydrofuranyl, tetrahydropyran-2-yl, tri(-lower alkyl)silyl or lower alkyl radical, X is a carbonyl, hydroxymethylene or (lower alkanoyl) oxymethylene radical V is a methylene, hydroxymethylene (lower alkanoyl) oxymethylene, tetrahydrofuranyloxymethylene, tetrahydropyran-2-yloxymethylene or tri-(lower alkyl)silyloxymethylene radical, Y is an ethylene, cis vinylene or transvinylene group, Z is an ethylene, cis vinylene, trans-vinylene or ethynylene radical, the wavy lines denote the alternative R, S stereochemical configurations, the dotted line indicates an optional double bond, m is an integer greater than 2 and less than 5 and $R_8$ is an alkyl group containing 3–5 carbon atoms or cycloalkyl group containing 5–7 carbon atoms.

British Pat. No. 1,492,426 describes compounds of the structural formula.

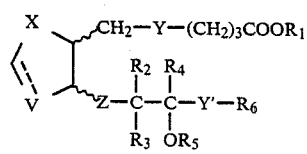

wherein $R_1$, $R_2$ and $R_3$ are hydrogen or an alkyl radical containing from 1 to 7 carbon atoms; $R_4$ is an alkyl radical containing from 1 to 7 carbon atoms; $R_5$ is hydrogen, an alkyl radical containing from 1 to 7 carbon atoms or an alkanoyl radical containing from 1 to 7 carbon atoms; $R_6$ is an alkyl radical containing from 2 to 4 carbon atoms or a cycloalkyl radical containing from 5 to 7 carbon atoms; X is carbonyl or hydroxymethylene; V is methylene, hydroxymethylene or alkanoyloxymethylene wherein the alkanoyl radical contains from 1 to 7 carbon atoms; or when X is carbonyl; V may also be a radical of the formula

=CH in which the bond represented by the dotted line in the general formula is present; Y is ethylene or vinylene; Y' is vinylene, ethynylene or the group

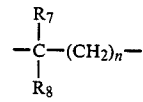

wheren n is 0 to 1 and $R_7$ and $R_8$ are hydrogen or an alkyl radical containing from 1 to 7 carbon atoms; Z is ethylene, vinylene or ethynylene; and the wavy lines represent the alternative A or B stereochemical configuration or the epimeric mixture: U.S. Pat. No. 4,499,296 describes the compounds of the formula.

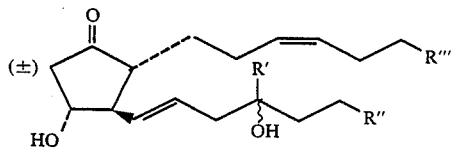

wherein R''' represents hydroxymethyl, hydroxyacetyl or —$CO_2R''''$ wherein R'''' represents hydrogen or lower alkyl containing 1 to 6 carbon atoms; R' represents lower alkyl containing 1 to 6 carbon atoms, vinyl or ethynyl; R'' represents cycloalkyl containing 3 to 5 carbon atoms; and the wavy line represents optional R,S stereochemistry.

European Patent Application No. 84 1136 76.5 describes prostaglandins of the formula I

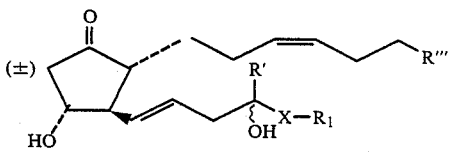

wherein X represents cis or trans —CH=CH—, —C≡C—, methylene or ethylene; $R_1$ represents a cycloalkyl group of the formula

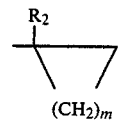

where
m is 1 to 3 inclusive
$R_2$ represents hydrogen or lower alkyl with the proviso that the sum of the carbon atoms in X and $R_1$ is 7 or less.
R' represents lower alkyl containing 1 to 6 carbon atoms, vinyl or ethynyl; and R''' is as defined above.

DETAILED DESCRIPTION OF THE INVENTION

This invention encompasses a compound of the formula I

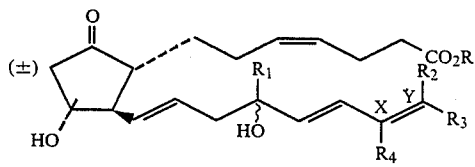

wherein R represents hydrogen or lower alkyl having 1 to 6 carbon atoms; $R_1$ represents hydrogen, vinyl, or lower alkyl having 1 to 4 carbon atoms and the wavy line represents R or S stereochemistry; $R_2$, $R_3$, and $R_4$ are hydrogen or lower alkyl having 1 to 4 carbon atoms or $R_2$ and $R_3$ together with carbon Y form a cycloalkenyl having 4 to 6 carbon atoms or $R_3$ or $R_4$ together with carbons X and Y form a cycloalkenyl having 4 to 6 carbons.

By lower alkyl is meant straight or branched chain alkyls such as methyl, ethyl, propyl, isopropyl, butyl, secondary butyl or tertiary butyl, pentyl, or hexyl with the indicated limitation of the number of carbon atoms.

A preferred embodiment is when $R_3$ and $R_4$ together with carbons X and Y form a cyclopentenyl ring. These compounds are preferred because of their exceptionally high $ED_{50}$ for diarrhea to $ED_{50}$ for antisecretory activity ratio.

Compounds of this invention are prepared by the following reaction scheme A

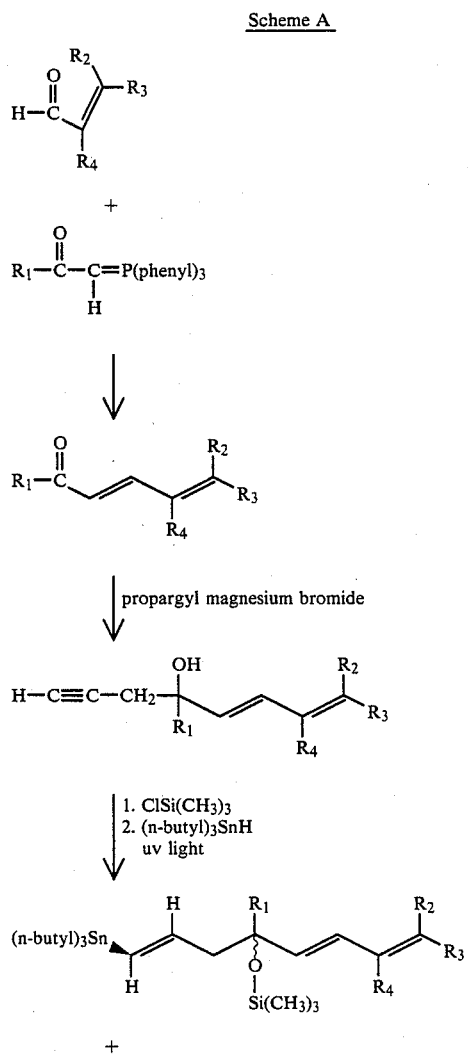

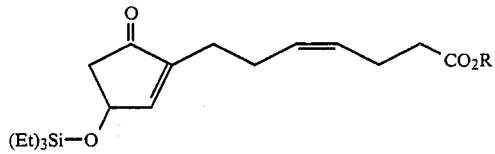

1. n-BuLi/Cu—C≡C—$CH_2$—$CH_2$—$CH_3$/ hexamethyl phosphorous triamide
2. Reaction with acetic acid/tetrahydrofuran/water Compounds of Formula I The general reaction is decribed in U.S. Pat. Nos. 4,322,543 and 4,271,314. These patents also describe methods of varying R from hydrogens, methyl, ethyl, isopropyl, butyl and the like. The tetraenyl prostaglandins of this invention are prepared according to the methods described for making the more saturated counterparts.

Regardless of the route of administration selected, the novel compounds of the invention are formulated into pharmaceutically acceptable dosage forms by conventional methods known to the pharmaceutical art.

The compounds can be administered in such oral unit dosage forms as tablets, capsules, pills, powders, or granules. They also may be administered intraperitoneally, subcutaneously, or intramuscularly, using forms known in the pharmaceutical art. In general, the preferred form of administration is oral. An effective but non-toxic quantity of the compound is employed in treatment. The dosage regimen for cytoprotection by the compounds of this invention is selected in accordance with a variety of factors including the type, age, weight, sex, and medical conditions of the patient, the organ to be protected, the route of administration and the particular compound employed. An ordinarily skilled physician will readily determine and prescribe the effective amount of the cytoprotective agent required to prevent or arrest the progress of the condition. In so proceeding, the physican could employ relatively low dosages at first, subsequently increasing the dose until a maximum response is obtained. Dosages of the compounds of the invention are ordinarily in the area of 0.01 to 10,000 ug/kg.

The cytoprotective utility of compounds of this invention are illustrated by standard test which show their ability to reduce ethanol-induced gastric lesions.

0.5 mg/kg is orally administered to adult 180–220 gram male Charles River rats which have been deprived of food for 24 hours. Thirty minutes layer 1.0 ml of absolute ethanol is administered intragastrically. The rats are sacrificed sixty minutes after alcohol administration and the gastric mucosae are visually examined for the presence of lesions. The number and severity of lesions are scored. A compound is judged active if it provides a statistically significant reduction in the number and/or severity of lesions compared to the control group.

The standard test used to detect gastric antisecretory activity is described as follows.

Adult female beagle dogs weighing 6–11 kg. are prepared with whole stomach simple Thomas-type gastric cannulas.

Following full recovery from the surgical implantation of the gastric cannula, the dogs are trained to stand quietly, though fully conscious, in Pavlov-type dog restraining slings and are accustomed to intravenous histamine infusion.

Experiments are initiated by depriving dogs of food, but not water, for 18 hours. With an initial infusion of 0.15M sodium chloride, at a constant rate of 6.5 ml/hr, gastric secretions collected in plastic bottles affixed to the cannula, are taken at 15 minute intervals and measured for volume to the nearest 0.1 ml. Following a 30–45 minute basal secretion period, the collection bottles are removed, dosing plugs inserted, and compound administered. A 3.0 ml saline which follows immediately.

After the end of a 30 minute drug absorption period the stomachs are emptied, collection bottles again attached, and the collections, resumed at 30 minute intervals. Simultaneously, the saline infusion is replaced with a continuous intravenous infusion of histamine dihydrochloride in saline at 15 μg/kg/hr for four hours. Gastric samples are analysed for pH and titratable acidity determinations.

An analysis of the data for each measured or derived variable compares observations recorded following treatment with variables obtained for the same group of animals receiving histamine stimulation alone. Three parameters, gastric juice volume (ml/30 min), acid concentration (mEq/L), and total acid output (mEq/30 min) are analyzed individually. The data thus obtained are analyzed using interval-by-interval paired Student's t-test or two-way analysis of variance to achieve an indication of potency and duration of action. Percentage inhibition is calculated using pooled mean values for the four hour treatment period. Duration of activity is defined as the length of time of significant inhibition.

Diarrhea is an undesirable side effect commonly associated with antisecretory and cytoprotective prostaglandins. Diarrheogenic activity is demonstrated by the following standardized test. Groups of six adult male Charles River rats, weight range 180 to 200 grams, are fasted for 24 hours prior to administering the test substance. The prostaglandin to be tested is adminstered intragastrically in iso-osmotic phosphate buffer at a volume of 10 ml/kg at doses ranging from 100 to 3000 microgram/kg. Control animals receive only the vehicle. The rats are placed in individual wire mesh cages and the trays lined with brown paper. Diarrhea is assessed at hourly intervals on an all or none basis for up to eight hours after administration of the prostaglandin. Diarrhea is defined as any loose or water stool. $ED_{50}$ values are assessed for each hourly diarrheogenic response.

The Compound of Examples 1 and 2 have the following results:

| | Antisecretory Activity Meal Stimulated Pavlov Pouch $ED_{50}$(meg/kg) | Diarrhea Assay Rat (iv) $ED_{50}$(meg/kg) | Thrapeutic Index $ED_{50}$diarrhea/ $ED_{50}$antisecretory |
|---|---|---|---|
| Example 1 | 0.02 | 3200 | 160,000 |
| Example 2 | 0.05 | 3200 (inactive) | |

The following examples illustrate the present invention and are not intended to limit the invention in spirit or scope. Temperatures are in degrees centigrade unless otherwise indicated.

EXAMPLE 1

1-Cyclopentene Methanol

Lithium Aluminum Hydride (1.69 parts) were suspended in 100 parts by volume of anhydrous tetrahydrofuran and the suspension was placed under a nitrogen atmosphere at room temperature.

The suspension was stirred and 5.0 parts of 1-cyclopentene carboxylic acid in 100 parts by volume of anhydrous ether were added over a 30 minute period. The reaction mixture was stirred for 1 hour after the completion of the addition. A 1N hydrochloric acid solution was added until there was no longer an evolution of gas. The reaction mixture was extracted with an ether/ethyl acetate mixture, the extracts were washed two times with potassium carbonate, two times with water and one time with saturated NaCl. The ether layer was dried over anhydrous sodium sulfate, the sodium sulfate removed by filtration, and the ther removed by evaporation at reduced pressure to provide 1-cyclopentene methanol.

1-Cyclopentene Carboxaldehyde

Pyridinium chlorochromate (16.1 parts) was suspended in 200 parts by volume of methylene chloride and 5 parts of 1-cyclopentene methanol in 25 parts by volume of methylene chloride were added dropwise. The reaction mixture was stirred for one hour and diluted with water and extracted with ether. The other extracts were dried over anhydrous sodium sulfate, separated, and the ther removed under reduced pressure to provide 1-cyclopentene carboxaldehyde.

4-(1-Cyclopentene)-3-trans-buten-2-one 2.7 parts of the above aldehyde and 11.1 parts of triphenylphosphoranylidene-2-propanone in 100 parts by volume of toluene were refluxed for about 16 hours. The solvent was removed by distillationat atmospheric pressure. The residue was extracted with hexane several times. The hexane extracts were combined, filtered and evaporated to a small volume. The residue was chromatographed on silica gel with 8% ethyl acetate in hexane as eluent to provide 1.3 parts of a light yellow oil which is 4-(1-cyclopentene)-3-trans-buten-2-one.

To 0.146 parts by volume of magnesium in 25 parts by volume of tetrahydrofuran under argon is added a small amount of propargyl bromide and mercuric chloride to initiate reaction. Once the reaction is started, 0.714 parts of propargyl bromide and 0.770 parts of 4-(1-cyclopentene)-3-trans-buten-2-one in 50 parts by volume of tetrahydrofuran is added dropwise so as to maintain reflux. Upon completion of the reaction, the reaction mixture is cooled to room temperature and poured into a mixture of ether and 1N HCl. The aqueous layer is extracted twice with ether. The ether extracts are combined and washed 3 times with water and one time with saturated sodium chloride solution, dried over anhydrous sodium sulfate, filtered, and evaporated to provide a residual oil. The residual oil is distilled under high vacuum to provide 4-methyl-4-hydroxy-6-(1'-cyclopentene)-hex-5E-en-1-yne.

To a solution of 1.1 parts of this material in 10 parts by volume of dimethylformamide containing 1 part of imidazole is added 0.756 parts of trimethylsilyl chloride. After 30 minutes of stirring, the reaction mixture is poured into an ether/water mixture, extracted with more ether and the organic layers are combined and washed with water and saturated sodium chloride solution. The solvent is removed and the residual oil is chromatographed on silica gel with 5% ethyl acetate/hexane to provide 4-methyl-4-trimethylsilyloxy-6-(1'-cyclopentene)-5E-en-1-yne. 0.715 Parts of this material is reacted with 0.838 parts of tri-n-butyl tin hydride at 20° C. catalyzed with ultraviolet light and a few milligrams of (AIBN) azobisisobutyronitrite to provide a compound of the formula.

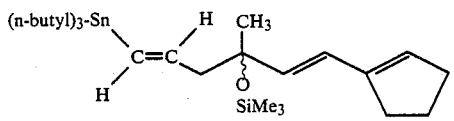

1.6 parts of this trans vinyl tin product is dissolved in 3 parts by volume of tetrahydrofuran, cooled to −60° C. and 8.86 parts by volume of 1.66 molar n-butyl lithium is added while maintaining the reaction mixture in an argon atmosphere. After 1 hour at −60° C. a solution of 0.388 parts of copper pentyne and 0.979 parts of hexamethylphosphorous triamide in 15 parts by volume of ether are added. After 10 minutes a solution of 0.528 parts of 7-(3-triethylsilyloxy-5-oxocyclopent-1-ene)-hept-4-cis-enoate (U.S. Pat. No. 4,271,314) in 15 parts by volume of ether are slowly added. The solution is stirred for one hour and poured into a mixture of ether and 1 N hydrochloric acid. The ether layer is separated, washed twice with water, filtered, dried over sodium sulfate and the ether is removed by evaporation at reduced pressure. The residual oil is chromatographed on silica gel (87% ethyl acetate/hexane as eluent) to give the protected prostaglandin. This material is dissolved in 5 parts by volume of a 3:1:1 mixture of acetic acid; tetrahydrofuran; water and is allowed to stand at room temperature for 30 minutes. The solution is diluted with ether, washed with water five times, and dried over anhydrous sodium sulfate. The ether is removed by evaporation at reduced pressure and the residual oil is chromatographed on silica gel (60% ethyl acetate/hexane as eluent) to provide methyl 7-[3α-hydroxy-2β-(4-hydroxy-4-methyl-6-(1'-cyclopentenyl)-1,5-trans,trans-hexadienyl)-5-oxycyclopentane]-1-α-hept-4-cis-enoate having the following formula

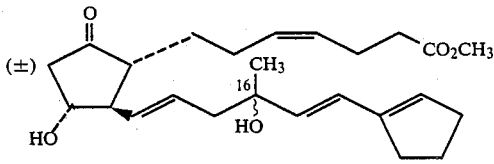

The racemic mixture is separated by chromatography on 65% ethyl acetate/hexane to provide racemates A and B having the indicated configuration at C-16.

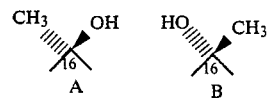

EXAMPLE 2

Following the procedures in Examples 1 and using equivalent quantities:
3-methyl-2-butenol is converted to
3-methyl-2-butene carboxaldehyde which in turn is reacted with triphenylphosphoranyliden-2-propanane to provide 6-methyl-hept-3,5-diene-2-one.

Reaction of this ketone with propargyl magnesium bromide provides 4,8-dimethyl-4-hydroxy non-7-ene-1-yne. This alcohol is protected with trimethylsilyl chloride and converted to trans vinyl tin derivative of 4,7-dimethyl-4-trimethylsiloxy-non-8-ene-1-yne which is converted to the corresponding prostaglandin by the methods described in U.S. Pat. Nos. 4,322,543 and 4,271,314 to provide methyl 7-[3α-hydroxy-2β-(4-hydroxy-4,8-dimethyl-1,5,7-trans,trans-nonatrienyl-5-oxocyclopentane]-1α-hept-4-cis-enoate having the formula

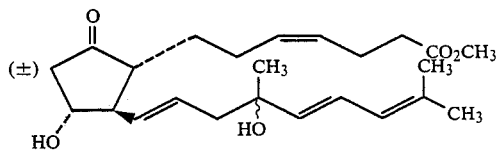

The racemates are separated by chromatography on silica gel using 60% ethyl acetate/hexane as eluent.

What is claimed is:

1. A compound according to the formula:

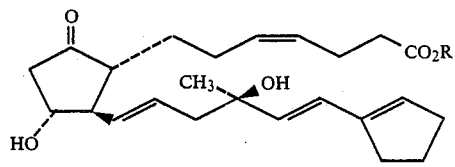

wherein R represents hydrogen or lower alkyl having 1-6 carbon atoms.

2. A pharmaceutical composition for treating gastric lesions in mammals comprising a therapeutically effective but non-toxic amount of a compound according to claim 1 as the active agent.

3. A method of treating gastric lesions comprising administering to a mammal in need of such treatment a therapeutically effective but non-toxic amount of a compound according to claim 1.

* * * * *